(12) United States Patent
Rosen et al.

(10) Patent No.: US 9,603,844 B2
(45) Date of Patent: Mar. 28, 2017

(54) COMPOSITIONS AND METHODS FOR TREATING MAMMARY TUMORS

(71) Applicant: GEORGETOWN UNIVERSITY, Washington, DC (US)

(72) Inventors: Eliot M Rosen, Fairfax, VA (US); York A Tomita, Bethesda, MD (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 14/437,484

(22) PCT Filed: Oct. 22, 2013

(86) PCT No.: PCT/US2013/066090
§ 371 (c)(1),
(2) Date: Apr. 21, 2015

(87) PCT Pub. No.: WO2014/066330
PCT Pub. Date: May 1, 2014

(65) Prior Publication Data
US 2015/0265590 A1 Sep. 24, 2015

Related U.S. Application Data

(60) Provisional application No. 61/716,777, filed on Oct. 22, 2012.

(51) Int. Cl.
| | | |
|---|---|---|
| *A61K 31/445* | (2006.01) | |
| *A61K 38/00* | (2006.01) | |
| *A61K 31/4453* | (2006.01) | |
| *A61K 45/06* | (2006.01) | |
| *A61K 31/12* | (2006.01) | |
| *A61K 31/135* | (2006.01) | |
| *A61K 31/137* | (2006.01) | |
| *A61K 31/138* | (2006.01) | |

(Continued)

(52) U.S. Cl.
CPC .......... *A61K 31/4453* (2013.01); *A61K 31/12* (2013.01); *A61K 31/135* (2013.01); *A61K 31/137* (2013.01); *A61K 31/138* (2013.01); *A61K 31/404* (2013.01); *A61K 31/421* (2013.01); *A61K 31/4535* (2013.01); *A61K 31/55* (2013.01); *A61K 31/565* (2013.01); *A61K 45/06* (2013.01)

(58) Field of Classification Search
CPC .. A61K 31/4453; A61K 31/12; A61K 31/135; A61K 31/137; A61K 31/138; A61K 31/404; A61K 31/421; A61K 31/4535; A61K 31/55; A61K 31/565; A61K 45/06
USPC ................................................ 514/317, 19.4
See application file for complete search history.

(56) References Cited

PUBLICATIONS

Lack et al, Targeting the Binding Function 3(BF3)site of the Human Androgen Receptor through Virtual Screening, Journal of Medicinal Chemistry, 2011, 54(24), p. 8563-8573.*

* cited by examiner

*Primary Examiner* — T. Victor Oh
(74) *Attorney, Agent, or Firm* — Morgan, Lewis & Bockius LLP

(57) ABSTRACT

The present invention provides methods of inhibiting abnormal growth of cells, with the methods comprising contacting the cells with at least one of the sensitizing compounds disclosed herein in an amount sufficient to inhibit cell growth. The present invention also provides methods of treating and/or reducing the likelihood of being diagnosed with breast cancer, with the methods comprising administering to a subject in need of treatment thereof at least one of the sensitizing compounds disclosed herein.

10 Claims, 20 Drawing Sheets

(51) Int. Cl.
*A61K 31/404* (2006.01)
*A61K 31/421* (2006.01)
*A61K 31/4535* (2006.01)
*A61K 31/55* (2006.01)
*A61K 31/565* (2006.01)

MCF-7

| NUCLEAR EXTRACT | + | + | + | + | + | + | + | + | + | + |
| 4631P/1(μM) | – | – | – | – | – | 1 | 0.1 | 1 | 2 | 5 |
| HOT ERE | + | + | + | + | + | + | + | + | + | + |
| E2 (10nM) | – | + | + | – | + | – | + | + | + | + |
| COLD ERE | – | – | + | – | – | – | – | – | – | – |

MCF-7

| NUCLEAR EXTRACT | + | + | + | + | + | + | + | + | + | + |
| 4631(μM) | – | – | – | – | – | 0.1 | 1 | 1 | 2 | 5 |
| HOT ERE | + | + | + | + | + | + | + | + | + | + |
| E2 (10nM) | + | – | + | + | + | + | + | + | + | + |
| COLD ERE | – | – | – | + | – | – | + | – | – | – |
| ATNRI-ERα | – | – | + | + | + | + | + | + | + | + |

COMPOSITIONS AND METHODS FOR TREATING MAMMARY TUMORS

STATEMENT REGARDING FEDERALLY SPONSORED RESEARCH OR DEVELOPMENT

Part of the work performed during development of this invention utilized U.S. Government funds under United States Public Health Service Contract Nos. R01-CA150646 and R01-CA08599. The U.S. Government has certain rights in this invention.

BACKGROUND OF THE INVENTION

Field of the Invention

The invention relates to compositions and methods for treating estrogen-resistant breast cancer cells.

Background of the Invention

Estrogen receptor-alpha (ER-α) is a member of the nuclear receptor superfamily of ligand activated transcription factors, characterized by: an N-terminal transactivation domain (AF-1), a conserved C-terminal activation domain (AF-2), which overlaps with the ligand binding domain (LBD), a sequence-specific DNA-binding domain (DBD), and a hinge region located between the DBD and AF-2 regions.

Most breast cancers (BCs) (≅70%) are initially estrogen receptor-positive (ER+) and thus potentially suitable for anti-estrogen therapy. Despite being ER+, 50% of patients with advanced breast cancer who receive Tamoxifen (Tam) fail to respond, and all patients with metastatic breast cancer eventually develop resistance to Tam. In addition, many patients (≅40%) who receive Tam as adjuvant therapy will relapse and die of disease. The causes of resistance to different anti-estrogens are not identical, but cross-resistance is common. In most cases of acquired anti-estrogen (E2) resistance, breast cancer cells retain ER and thus may be amenable to novel approaches to target ER.

BRCA1 is a strong inhibitor of E2-stimulated ER-α activity via a direct physical interaction with the AF-2 activation domain of ER-α. In mice, BRCA1 expression is widespread, but it is especially increased in rapidly proliferating cells in compartments that are also undergoing differentiation, including mammary epithelial cells during puberty and pregnancy. BRCA1 also represses ligand-independent activation of ER-α, since BRCA1-siRNA can stimulate ER-α activity in the absence of estrogen. This finding suggests that the endogenous levels of BRCA1 are sufficient to inhibit basal activity levels of ER-α. Further studies have documented that BRCA1 broadly inhibits E2-stimulated gene expression and blocks E2-stimulated proliferation of ER-α positive human breast cancer cells. BRCA1 has been detected at the estrogen response element site of estrogen-regulated promoters (pS2 and cathepsin D), and exposure to E2 causes a rapid loss of BRCA1 from this site. Various breast cancer-associated BRCA1 mutations abrogate or greatly lessen the ability of BRCA1 to inhibit ER-α, suggesting that this function is essential for breast cancer suppression. Finally, it has recently been shown BRCA1 can inhibit the activity of aromatase (CYP19A1), a cytochrome P450 enzyme that mediates the conversion of androgens into estrogens, in epithelial cells and adipocytes.

Mutations of the BRCA1 gene account for about half of all hereditary breast cancer. In 30-40% of sporadic breast cancer, BRCA1 expression is absent or reduced, suggesting a wider role in breast cancer. While many studies on BRCA1 focus on its roles in DNA repair, it also has a major role in regulating ER activity, loss of which confers hypersensitivity to E2 and mammary cancer development in mice. BRCA1 knockdown stimulates the ER agonist activity of Tam, and Tam promotes mammary cancer development in BRCA1-deficient mice. In addition, BRCA1-siRNA can cause Tam-resistance due to altered recruitment of co-regulators by ER. These observations suggest that the early stages of BRCA1-dependent mammary tumorigenesis could be E2-dependent, and thus it may be possible to prevent or treat BRCA1-mutant breast cancers using an agent that can mimic the ability of BRCA1 to inhibit ER-α activity.

SUMMARY OF THE INVENTION

The present invention provides methods of inhibiting abnormal cell growth, with the methods comprising administering to the cells at least one sensitizing compound in an amount sufficient to inhibit abnormal cell growth, with the at least one sensitizing compound being:

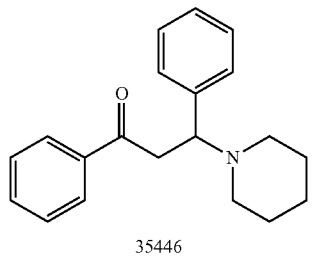

35446

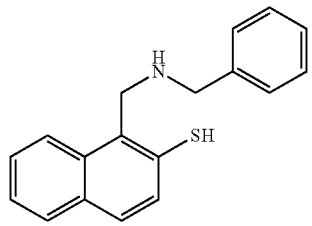

81747

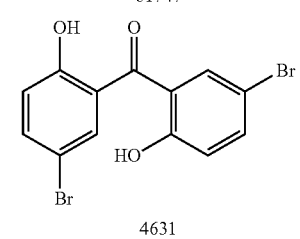

4631

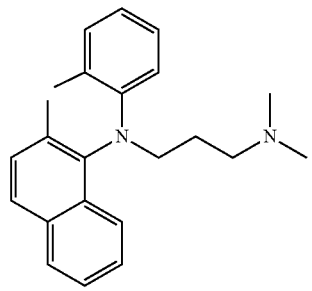

18891

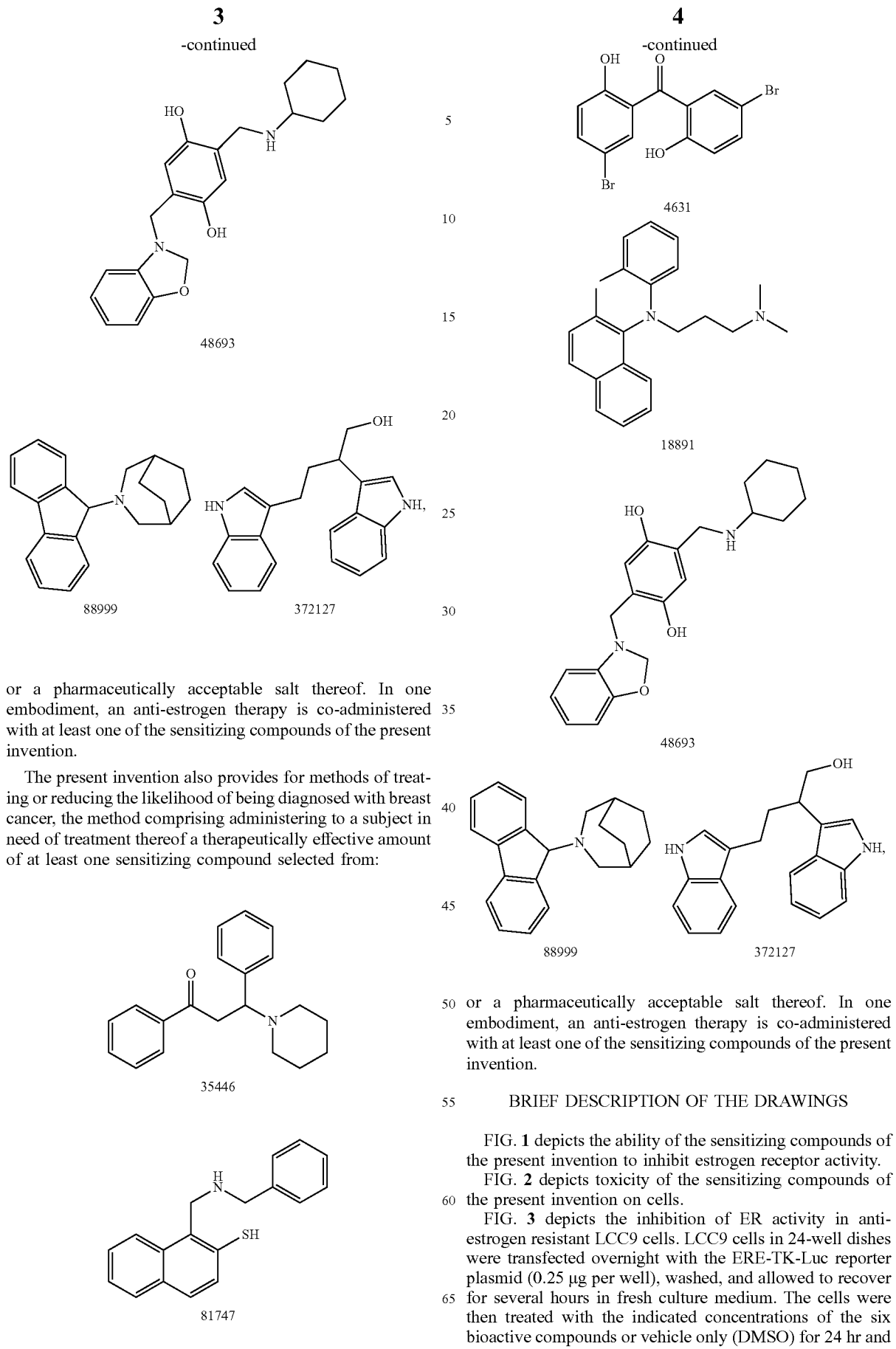

or a pharmaceutically acceptable salt thereof. In one embodiment, an anti-estrogen therapy is co-administered with at least one of the sensitizing compounds of the present invention.

The present invention also provides for methods of treating or reducing the likelihood of being diagnosed with breast cancer, the method comprising administering to a subject in need of treatment thereof a therapeutically effective amount of at least one sensitizing compound selected from:

or a pharmaceutically acceptable salt thereof. In one embodiment, an anti-estrogen therapy is co-administered with at least one of the sensitizing compounds of the present invention.

DETAILED DESCRIPTION OF THE INVENTION

Figure 1A:
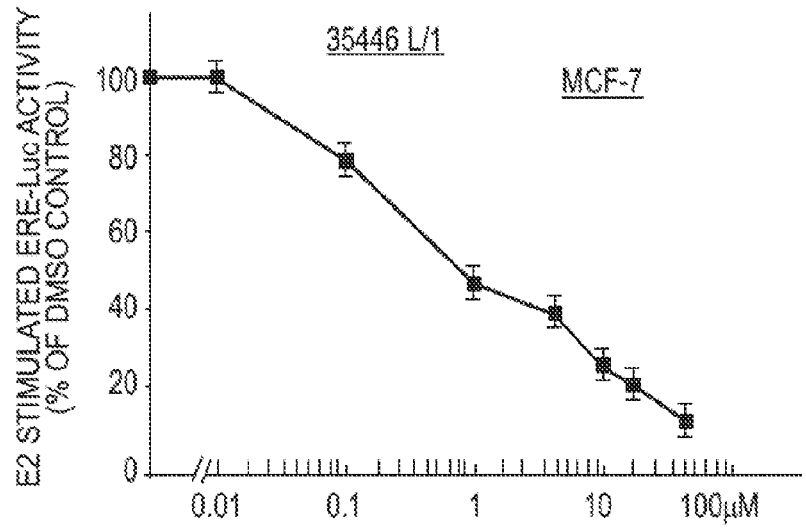
FIG. 1 depicts the ability of the sensitizing compounds of the present invention to inhibit estrogen receptor activity.

The present invention provides methods of inhibiting abnormal cell growth, with the methods comprising administering to the cells at least one sensitizing compound in an amount sufficient to inhibit abnormal cell growth, with the at least one sensitizing compound being:

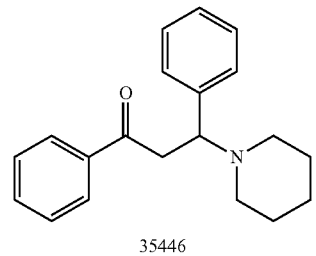

35446

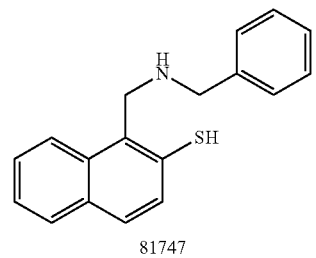

81747

-continued

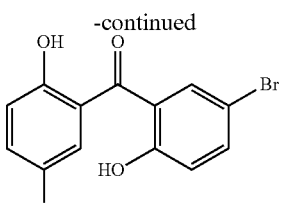
4631

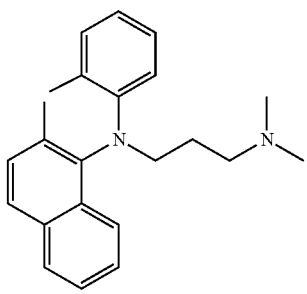
18891

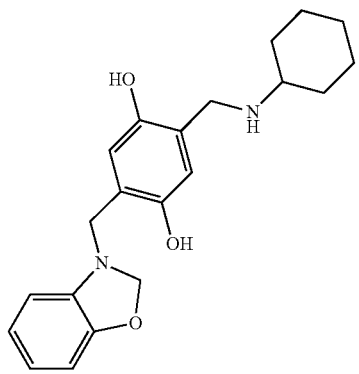
48693

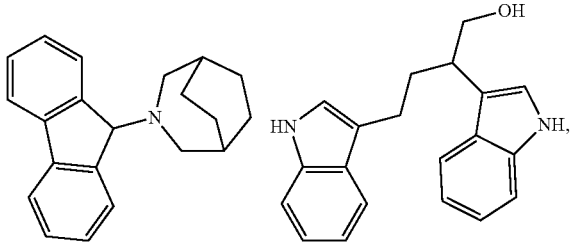
88999            372127 or a pharmaceutically acceptable salt thereof.

The phrase "pharmaceutically acceptable salt(s)," as used herein includes but is not limited to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions including, but not limited to, sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions that are acidic in nature are capable of forming base salts with various pharmacologically acceptable cations. Examples of such salts include alkali metal or alkaline earth metal salts and, particularly, calcium, magnesium, sodium lithium, zinc, potassium, and iron salts.

As used herein and unless otherwise indicated, the term "pharmaceutically acceptable prodrug" means a derivative of a compound that can hydrolyze, oxidize, or otherwise react under biological conditions, in vitro or in vivo, to provide the compound. Examples of prodrugs include, but are not limited to, compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include but are not limited to compounds that comprise oligonucleotides, peptides, lipids, aliphatic and aromatic groups, or NO, $NO_2$, ONO, and $ONO_2$ moieties. Prodrugs can typically be prepared using well known methods, such as those described in Burger's Medicinal Chemistry and Drug Discovery, pp. 172, 178, 949, 982 (Manfred E. Wolff ed., 5th ed. 1995), and Design of Prodrugs (H. Bundgaard ed., Elsevier, New York 1985).

As used herein and unless otherwise indicated, the terms "biohydrolyzable amide," "biohydrolyzable ester," "biohydrolyzable carbamate," "biohydrolyzable carbonate," "biohydrolyzable ureide," "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, lower acyloxyalkyl esters (such as acetoxylmethyl, acetoxyethyl, aminocarbonyloxy-methyl, pivaloyloxymethyl, and pivaloyloxyethyl esters), lactonyl esters (such as phthalidyl and thiophthalidyl esters), lower alkoxyacyloxyalkyl esters (such as methoxycarbonyloxy-methyl, ethoxycarbonyloxyethyl and isopropoxycarbonyloxyethyl esters), alkoxyalkyl esters, choline esters, and acylamino alkyl esters (such as acetamidomethyl esters). Examples of biohydrolyzable amides include, but are not limited to, lower alkyl amides, amino acid amides, alkoxyacyl amides, and alkylaminoalkyl-carbonyl amides. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, "abnormal cell growth" is used to mean a condition in which cells proliferate faster than normal or would proliferate uncontrollably without intervention. The cells may appear morphologically normal or the cells may be abnormal. As used herein, the cells can be in culture or can be part of a tissue, organ or organism, such as, but not limited to a human. The cells may be normal or abnormal, such as, but not limited to, malignant or benign cancer cells. Thus, in one embodiment, the combination of compounds is administered to neoplastic cells in an organism. In a specific embodiment, at least one combination of compounds of the present invention is administered to neoplastic mammary cells. The mammary cells to which the combination of compounds is administered may or may not be responsive to anti-estrogen therapy. In another embodiment, the combination of compounds is administered to neoplasms, such as, but not limited to, neoplasms of the blood-forming organs, the liver, pancreas, thyroid, andrenals, pituitary, ovaries, testicles, prostate, central nervous system (including brain, spinal column), bone, connective tissue, lungs, the gastrointestinal system (esophagus, stomach, colon, rectum, etc.), connective tissue, uterus, mucous membranes, mouth and tongue, the lining of the peritoneum, the lymphatics and sensory organs.

The methods of the present invention relate to inhibiting abnormal cell growth and/or inducing cell cycle arrest by administering at least one of the compounds of the present invention. The methods may also relate to inducing apoptosis in the cells to which at least one of the compounds of the present invention is administered.

As used herein, the term "administer" or "administering" is used to mean introducing at least one of the compounds of the present invention to a cell or group of cells, such that at least one of the compounds of the present invention can exert a biological effect on the cell or group of cells. Of course, "administration" can also include administering a combination of compounds. Thus, administration may be in the form of dosing an organism with a compound or combination of compounds, such that the organism's circulatory system will deliver a compound or combination of compounds to the target cell or cells. Administration may also mean that a compound or combination of compounds is placed in direct contact with the cell or group of cells, such as topical administration of a compound or combination of compounds, or direct injection of the combination of compounds. Administration may also mean placing a compound or combination of compounds in cell culture medium and placing the cell or group of cells in contact with the dosed cell culture medium.

As shown in FIG. 1, the sensitizing compounds described herein can inhibit abnormal cell proliferation when administered on their own. Thus, the present invention is directed to methods of inhibiting abnormal cell growth comprising administering at least one of the sensitizing compounds of the present invention to cells exhibiting abnormal cell growth. In the alternative, the sensitizing compounds of the present invention also restore, or sensitize, cells to the effects of anti-estrogen compounds. Thus, in one embodiment of the present invention, at least one sensitizing compound described herein, or a pharmaceutically acceptable salt or prodrug thereof, is coadministered with an anti-estrogen compound to inhibit abnormal cell proliferation. In another embodiment of the present invention, at least one sensitizing compound described herein, or a pharmaceutically acceptable salt or prodrug thereof, is administered to the cells to inhibit abnormal cell proliferation.

As used herein, an anti-estrogen compound is a compound that at least partially inhibits or blocks the production and/or normal activity of estrogen. Some of the ways through which inhibition of estrogen's activity can be achieved include but are not limited to blocking the binding of estrogen to its receptor, blocking the binding of the estrogen/receptor complex to co-activators and increasing degradation of estrogen and/or its receptor, to name a few. There are traditionally three classes of anti-estrogen compounds well-known in the art: selective estrogen receptor modulators (SERMs) that generally bind to estrogen receptor to prevent estrogen from binding its receptor, selective estrogen receptor down-regulators (SERDs) that generally cause degradation of estrogen receptors, and aromatase inhibitors that generally block formation of estrogen from androgens. Examples of SERMs include but are not limited to clomifene, femarelle, ormeloxifene, raloxifene, tamoxifen, toremifene, lasofoxifene, afimoxifene, arzoxifene and bazedoxifene to name a few. Some of these SERMs have at least partial estrogen agonist activities, depending on the tissue or cell type to which the compound is administered. Examples of aromatase inhibitors include but are not limited to 1,4,6-androstatrien-3,17-dione, 4-androstene-3,6,17-trione, letrozole, exemestane, aminoglutethimide, vorozole, formestane, fadrozole testolactone, anastrozole and 4-hydroxyandrostenedione.

In one embodiment, the anti-estrogen compound that is co-administered with a sensitizing compound is a SERM. In another embodiment, the anti-estrogen compound that is co-administered with a sensitizing compound is a SERD. In another embodiment, the anti-estrogen compound that is co-administered with a sensitizing compound is an aromatase inhibitor.

In a more specific embodiment, the anti-estrogen compound that is co-administered with a sensitizing compound is a tamoxifen-like compound. As used herein, a tamoxifen-like compound is a compound that shares a similar chemical core as tamoxifen and exerts similar, if not identical, effects on cells in vitro or in vivo as tamoxifen. Tamoxifen is a well-known estrogen antagonist in breast tissue, and it is believed to exert agonist-type activities in endometrial tissue. As used herein, the chemical core of tamoxifen, which is well-known, has the characteristic triphenyl structure in which the three hydrogen atoms of 1-butene are substituted with three phenyl groups as shown in Formula I below.

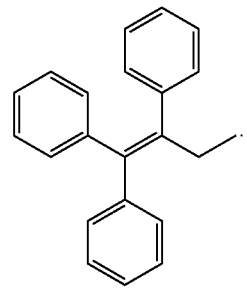

(I)

Tamoxifen itself has the chemical structure of Formula II, below.

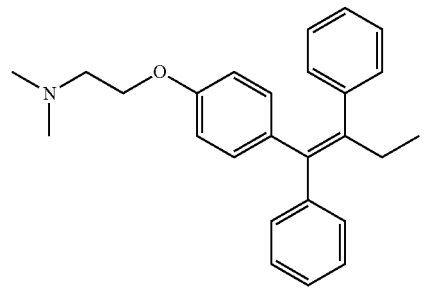

(II)

By way of non-limiting examples, tamoxifen-like compounds include but are not limited to tamoxifen, 4-hydroxytamoxifen and 4-desmethyl-4-hydroxytamoxifen.

In select embodiments, a combination of compounds is being administered to the cells, thus the individual compounds can also be said to be coadministered with one another. As used herein, "coadminister" indicates that each of the at least two compounds is administered during a time frame wherein the respective periods of biological activity or effects overlap. Thus the term coadminister includes sequential as well as coextensive administration of the individual compounds of the present invention. Accordingly, "administering" the combination of compounds according to some of the methods of the present invention includes sequential as well as coextensive administration of the individual compounds of the present invention. Likewise, the phrase "combination of compounds" indicates that the individual compounds are coadministered, and the phrase "combination of compounds" does not mean that the compounds must necessarily be administered contemporaneously or coextensively. In addition, the routes of administration of the individual compounds need not be the same.

The present invention also provides methods of treating breast cancer, with the methods comprising administering to a subject in need thereof a therapeutically effective amount of at least one sensitizing compound described herein, or a pharmaceutically acceptable salt or prodrug thereof.

As used herein and unless otherwise indicated, the phrase "therapeutically effective amount" of a compound or combination of compounds of the invention is measured by the therapeutic effectiveness of a compound of the invention, wherein at least one adverse effect of a disorder is ameliorated or alleviated.

The terms "treat" and "treatment" refer to an amelioration of a disease or disorder, or at least one discernible symptom thereof that may or may not be associated abnormal cell proliferation, such as cancer. In another embodiment, "treatment" or "treat" refers to an amelioration of at least one measurable physical parameter, not necessarily discernible by the patient. In yet another embodiment, "treatment" or "treat" refers to inhibiting the progression of a disease or disorder, either physically, e.g., stabilization of a discernible symptom, physiologically, e.g., stabilization of a physical parameter, or both. In yet another embodiment, "treatment" or "treat" refers to delaying the onset of a disease or disorder or delaying the onset of a physical parameter or symptom. In one specific embodiment, treatment refers to the application of the methods of the present invention to reduce, stall, or inhibit the growth of or proliferation of tumor cells. In another specific embodiment, treatment refers to the application of the methods of the present invention to induce apoptosis in tumor cells. The tumor cells may or may not respond to anti-estrogen therapy. In another specific embodiment, the tumor cells are resistant to anti-estrogen therapies. In a further embodiment, the anti-estrogen resistant tumor cells are mammary cancer cells.

When administration is for the purposes of "preventing" abnormal cell proliferation or preventing a cancer such as breast cancer ("prophylactic administration"), the compound or combination of compounds is provided in advance of any visible or detectable symptom. The prophylactic administration of the compound or combination of compounds serves to attenuate subsequently arising symptoms or physical parameters or reduce the possibility of symptoms from arising altogether. Thus, as used herein, the term "prevent" as used in connection with administering the compound or combination of compounds of the present invention, is used to indicate the timing of the administration, i.e., before a detectable symptom arises, rather than indicate a complete removal of the possibility of developing a condition associated with abnormal cell proliferation. The term "prevent" with respect to a disease or abnormal condition, can also mean that the methods of the present invention are intended to "reduce the likelihood" of the disease or abnormal condition, or a symptom thereof, from appearing or surfacing.

Thus present invention also provides for methods of reducing the likelihood of being diagnosed with breast cancer and also reducing the likelihood of a diagnosis of a recurrence of breast cancer, with the methods comprising administering to a subject in need of treatment thereof at least one sensitizing compound described herein or a pharmaceutically acceptable salt or prodrug thereof.

Due to the activity of the compounds of the invention, the compounds are advantageously useful in veterinary and human medicine. As described above, the compounds of the invention are useful for the treatment or prevention of diseases and disorders associated with abnormal cell proliferation.

The invention provides methods of treatment and prophylaxis by administration to a patient of a therapeutically effective amount of a compound or combination of compounds of the invention. The patient can be a mammal, including, but not limited to, an animal such a cow, horse, sheep, pig, cat, dog, mouse, rat, rabbit, guinea pig, etc., and a human or non-human primate.

Each of the individual compounds that are administered in conjunction with the methods of the present invention can be administered orally. Each of the individual compounds of the invention may also be administered by any other convenient route, for example, by infusion or bolus injection, by absorption through epithelial or mucocutaneous linings (e.g., oral mucosa, rectal and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer at least one of the compounds of the invention. Methods of administration of the individual compounds include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The preferred mode of administration is left to the discretion of the practitioner, and will depend, in part, upon the site of the medical condition. In most instances, administration will result in the release of the combination of compounds of the invention into the bloodstream.

In specific embodiments, it may be desirable to administer one or more compounds of the combination locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration of at least one of the compounds of the combination can be by direct injection at a specific site that is diseased or abnormal. In another embodiment, at least one of the compounds of the combination may be conjugated to an antibody that is specific towards an antigen on the abnormally proliferating cells.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of the invention can be formulated as a suppository, with traditional binders and vehicles such as triglycerides.

In another embodiment, the compounds of the invention can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, at least one of the compounds used in the methods of the invention can be delivered in a controlled release system. In one embodiment, a pump may be used (see Langer, supra; Sefton, 1987, CRC Crit. Ref. Biomed. Eng. 14:201; Buchwald et al., 1980, Surgery 88:507 Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled-release system can be placed in proximity of at least one a compound or compound of the combination, e.g., the liver, thus requiring only a fraction of the systemic dose (see, e.g., Goodson, in Medical Applications of Controlled Release, supra, vol. 2, pp. 115-138 (1984)). Other controlled-release systems discussed in the review by Langer, 1990, Science 249:1527-1533) may be used.

The present methods can also deliver a therapeutically effective amount of a compound or combination of compounds together with a suitable amount of a pharmaceutically acceptable vehicle so as to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. In one embodiment, when administered to a patient, the combination of compounds of the invention and pharmaceutically acceptable vehicles are sterile. Water and/or oils are one vehicle when the combination of compounds of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present combination of compounds, if desired, can also contain minor amounts of wetting or emulsifying agents, or pH buffering agents.

Each of the individual compounds to be administered can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in Remington's Science and Practice of Pharmacy (21st ed., Hendrickson, R., et al., Eds., Lippincott Williams & Wilkins, Baltimore, Md. (2006)), which is incorporated by reference.

Typically, when the individual compounds of the invention are administration intravenously, the compounds are in sterile isotonic aqueous buffered solutions. Where necessary, the individual compounds of the invention may also include a solubilizing agent. The individual compounds of the invention for intravenous administration may optionally include a local anesthetic such as lidocaine to ease pain at the site of the injection.

In one embodiment, individual compounds are supplied either together in a unit dosage form or separately. Regardless, compounds may be supplied, for example, as a dry lyophilized powder or water free concentrate in a hermetically sealed container such as an ampoule or sachette indicating the quantity of active agent. Where the compound or combination of compounds of the invention are to be administered by infusion, they can be dispensed, for example, with an infusion bottle containing sterile pharmaceutical grade water or saline. Where the compound or combination of compounds of the invention is administered by injection, an ampoule of sterile water for injection or saline can be provided so that the ingredients may be mixed prior to administration.

In one embodiment, the individual compounds can be administered orally. Compositions for oral delivery may be in the form of tablets, lozenges, aqueous or oily suspensions, granules, powders, emulsions, capsules, syrups, or elixirs, for example. Orally administered compositions may contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

The amount of each individual compounds to be administered will depend on the nature of the disorder or condition, and can be determined by standard clinical techniques. In addition, in vitro or in vivo assays may optionally be employed to help identify optimal dosage ranges for each of the components of the combination. The precise dose of each component to be employed will also depend on the route of administration and the seriousness of the disease or disorder, and a practitioner can determine these doses based upon each patient's circumstances. In general, however, suitable dosage ranges for oral administration are generally about 0.001 milligram to 200 milligrams of a compound of the invention per kilogram body weight. In specific embodiments of the invention, the oral dose for each component is 0.01 milligram to 70 milligrams per kilogram body weight, more specifically 0.1 milligram to 50 milligrams per kilogram body weight, more specifically 0.5 milligram to 20 milligrams per kilogram body weight, and yet even more specifically 1 milligram to 10 milligrams per kilogram body weight. The dosage amounts described herein refer to individual amounts administered.

In general, suitable dosage ranges for intravenous (i.v.) administration of individual components are 0.01 milligram to 100 milligrams per kilogram body weight, 0.1 milligram to 35 milligrams per kilogram body weight, and 1 milligram to 10 milligrams per kilogram body weight. In general, suitable dosage ranges for intranasal administration of the individual components are generally about 0.01 pg/kg body weight to 1 mg/kg body weight. In general, suppositories generally contain 0.01 milligram to 50 milligrams of a compound per kilogram body weight and may comprise active ingredient in the range of 0.5% to 10% by weight. Effective doses may be extrapolated from dose-response curves derived from in vitro or animal model test systems. Such animal models and systems are well known in the art.

The invention also provides pharmaceutical packs or kits comprising one or more containers filled with one or more compounds to be administered in practicing the methods of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In a certain embodiment, the kit contains more than one compound.

The examples herein are for illustrative purposes only and they are not intended to limit the scope of the invention in any way.

EXAMPLES

Material and Methods

ER-positive human breast cancer cells (MCF-7) were originally obtained from the American Type Culture Collection (ATCC, Manassas, Va.) and cultured as has been described in the literature. Briefly, cells were routinely cultured in DMEM plus 5% fetal calf serum, L-glutamine (5 mM), non-essential amino acids (5 mM), penicillin (100 U/ml), and streptomycin (100 µg/ml) (all obtained from BioWhittaker, Walkersville, Md.). Cultures were incubated at 37° C. in a humidified atmosphere containing 5% $CO_2$.

The wild-type BRCA1 expression vector was created by cloning the full-length BRCA1 cDNA into the pcDNA3 vector (Invitrogen, Carlsbad, Calif.), as described in the literature. The estrogen-responsive reporter ERE-TK-Luc is composed of the vitellogenin A2 estrogen-responsive enhancer (ERE) controlling a minimal thymidine kinase promoter (TK81) and luciferase in plasmid pGL2. The progesterone-responsive luciferase reporter MMTV-Luc has been described elsewhere in the literature.

The small interfering RNAs were the following: ER-α siRNA:Sense 5'-CAGGCACAUGAGUAACAAATT-3' and antisense 5'-UUUGUUACUCAU GUGCCUGAT-3' (catalog number: 43924220, Ambion/Life Technologies; and negative control-siRNA (catalog number: AM4461, Ambion). The efficacy of the ER-siRNA was validated by Western blotting. For siRNA treatments, subconfluent cells were treated with ER-specific or control siRNAs (final concentration of 100 nM) using siPORT Amine transfection reagent (Ambion), according to the manufacturer's instructions. Western blotting experiments showed that a minimum of 48 hr exposure to 100 nM of ER-siRNA was required to obtain a significant reduction (>75%) of the BRCA1 protein levels.

Subconfluent cells in 24-well dishes were transfected overnight with 0.25 µg of each indicated vector plus the ERE-TK-Luc reporter in serum-free DMEM containing Lipofectamine2000 (Life Technologies). The total transfected DNA was kept constant by addition of the appropriate control vector. The cells were washed, incubated in phenolphthalein-free DMEM containing 5% charcoal-stripped serum (obtained from the Tissue Culture Shared Resource of the Lombardi Comprehensive Cancer Center) (0.2 ml/well) with or without E2 (10 nM) and the indicated additional compound(s) for 24 hr, and harvested for luciferase assays. For each assay condition tested in each experiment performed, four replicate wells were tested. Values are presented as mean±SEMs. To determine the transfection efficiency, cultures were co-transfected with plasmid pRSV-β-gal (Promega Corporation, Madison, Wis.) to allow staining with X-gal reagent and visualization of transfected (blue-staining) cells.

Progesterone receptor (PR) transcriptional activity assays were carried out in T47D cells using the synthetic progestin R5020 (10 nM) to activate PR and the MMTV-Luc reporter as a readout for PR activity.

MTT assays were performed as described in the literature. This assay is based on the ability of intact mitochondria to convert MTT, a soluble tetrazolium salt, into an insoluble formazan precipitate, which is quantified by spectrophotometry after solubilization in DMSO. After the indicated cell treatments, cells in 96-well dishes were solubilized and assayed for MTT dye reduction, based on the difference between absorbance at 570 and 630 nm. Cell viability was expressed as the amount of dye reduction relative to untreated control cells. Cell viability values were calculated as means±SEMs for 10 replicate wells.

Cell proliferation assays were carried out using LCC2 and LCC9 cells using phenol red-free DMEM containing 5% charcoal-stripped serum (obtained from the Tissue Culture Shared Resource of the Lombardi Comprehensive Cancer Center) as the growth medium. Briefly, subconfluent proliferating cells were harvested using trypsin, counted, inoculated into 12-well dishes at $1\times10^4$ cells per well on day 0 and allowed to attach and recover for 24 hr, the cells were treated with the indicated agents at the indicated concentrations for up to five days, with daily refeeding with fresh medium and agents. Triplicate wells were counted by Coulter Counter on days 1, 3, and 5. For experiments utilizing siRNAs, cells were treated with the indicated siRNA (100 nM) starting on day −2, and fresh siRNA was added on days 0, 2, and 4. Values plotted are means±SEMs of three wells for each experimental condition tested.

Electrophoretic mobility shift assay (EMSA) and supershift assays were performed with double-stranded oligonucleotides containing a consensus estrogen response element (ERE) that were obtained from Santa Cruz Biotechnology (catalog number sc-2858, Santa Cruz, Calif.). The sequences of these ERE-containing oligonucleotides were as follows: sense, 5'-GGATCTAGGTCACTGT-GACCCCGGATC-3' and antisense, 3'-CCTAGATCCAGT-GACACTGGGGCCTAG-5'. The oligonucleotides were 3'-end-labeled with using a Biotin Kit, following the manufacturer's instructions (catalog number: 89818, Thermo Scientific, Rockford, Ill.

DNA binding reactions were performed using nuclear extracts of MCF-7 cells that had been treated without or with E2 (10 nM) and with the indicated compound at the indicated concentration(s) for 24-hr. After cell treatment, the cells were harvested and nuclear extracts were prepared using the NE-PER Nuclear and Cytoplasmic Extraction Reagents (catalog number: 78833, Thermo Scientific). Aliquots of nuclear extract protein (2 µg) were incubated with gel-shift binding buffer (LightShift Chemiluminescent EMSA Kit, Thermo Scientific, catalog number: 20148) for 30 min at 25° C. according to the manufacturer's instructions. After incubation, 40 fmol of biotin-labeled ERE-containing oligonucleotides were added, and the mixture was further incubated for 30 min at 25° C. The reaction products were loaded onto a 6% DNA retardation gel (Invitrogen). Electrophoresis was performed for 90-min at a constant voltage of 100V, and the gel was transferred onto a nylon membrane at 60 mV for 1-hr. Biotin labeled DNA was detected using the Chemiluminescent Nucleic Acid Detection Module (Thermo Scientific). To validate the specificity of binding, a 40-fold excess of unlabeled ("cold") oligonucleotide was added to one of the reactions along with the biotin-labeled ("hot") oligonucleotide.

Supershift assays were performed as described above, except that before addition of the hot ERE-containing oligonucleotide, nuclear extract samples were incubated with gel-shift binding buffer along with 2 µg of anti-ER IgG (rabbit polyclonal, HC-20, catalog number: sc-543, Santa Cruz) for 30 min at 25° C.

Immunoprecipitation (IP) was performed as follows. After the indicated transfections and/or treatments, cells were harvested, and whole cell extracts were prepared in IP buffer [10 mM Tris-HCl (pH 7.4), 150 mM NaCl, 1 mM EDTA, 1 mM EGTA, 1% Triton X-100, 0.5% IGEPAL CA-630 (Sigma, Catalog No. 18896), 10% glycerol, 1 mM sodium orthovanadate, and protease inhibitor cocktail (Santa Cruz Biotechnology, Santa Cruz, Calif.)]. Each IP was carried out using 2 µg antibody and 500 µg extract protein. The extracts were incubated with anti-ER antibody H184 (sc-7207, rabbit polyclonal IgG, Santa Cruz) or with a combination of anti-BRCA1 mouse monoclonals (Ab-1+ Ab-2+Ab-3, Calbiochem, San Diego, Calif.); the precipitated proteins were collected using protein A/G agarose (Santa Cruz). After low-speed centrifugation to remove the supernatant, the agarose was washed with PBS, collected in boiling sample buffer (Santa Cruz), and subjected to SDS-PAGE and Western blotting (see below). One half of the immunoprecipitated protein was used for Western blotting. For each experiment, a control immunoprecipitation using an equal quantity of normal mouse or rabbit IgG (Santa Cruz) was carried out.

For Western blotting, after the indicated treatment(s), cells were harvested, and whole-cell lysates were prepared using RIPA buffer (Santa Cruz). Equal aliquots of whole-cell protein (either 100 µg unprecipitated whole-cell lysate or one half of the precipitated protein from 500 µg whole-cell lysate) were electrophoresed on 4-12% SDS-polyacrylamide gradient gels, transferred to nitrocellulose membranes (Millipore, Bedford, Mass.), and blotted using primary antibodies directed against BRCA1 (C-20, rabbit polyclonal, 1:200 dilution; Santa Cruz), ER (F10, mouse monoclonal, sc-8002, 1:500; Santa Cruz), and actin (goat polyclonal, catalog item sc-1615, 1:400; Santa Cruz). The membranes were then blotted with the appropriate secondary antibodies (1:1000; Santa Cruz), and the blotted proteins were visualized using an electrochemiluminescence (ECL) detection system (Amersham Biosciences), with colored markers (Bio-Rad Laboratories, Hercules, Calif.) as molecular size standards.

Example 1

Effects of Sensitizing Compounds on Breast Cancer Cells

Tamoxifen-sensitive MCF-7 cells ("Tam-sensitive") were transfected overnight with an E2-responsive reporter (ERE-TK-Luc) and subsequently exposed to 10 nM of 17β-estradiol (E2, 10 nM) for 24 hours in the presence of the various concentrations of compound 35446-L/1. Luciferase activity was then assayed. FIG. 1A shows the results, with values being expressed as a percentage of the DMSO (vehicle)-treated control as means±SEMs of four replicate wells.

Figure 1B:
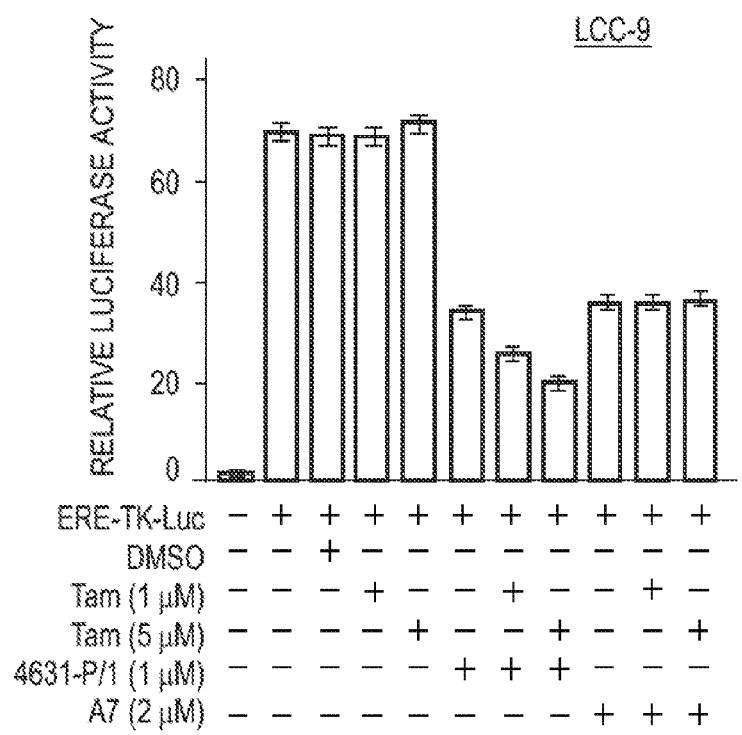

Tamoxifen-resistant LCC9 ("Tam-resistant") cells were transfected with ERE-TK-Luc and subsequently exposed to Tam±the sensitizing compounds for 24 hours. Luciferase activity was then assayed. FIG. 1B shows the results, with luciferase activity (related to cells not transfected with ERE-TK-Luc) being expressed as means±SEMs of four replicate wells.

Figure 1C:
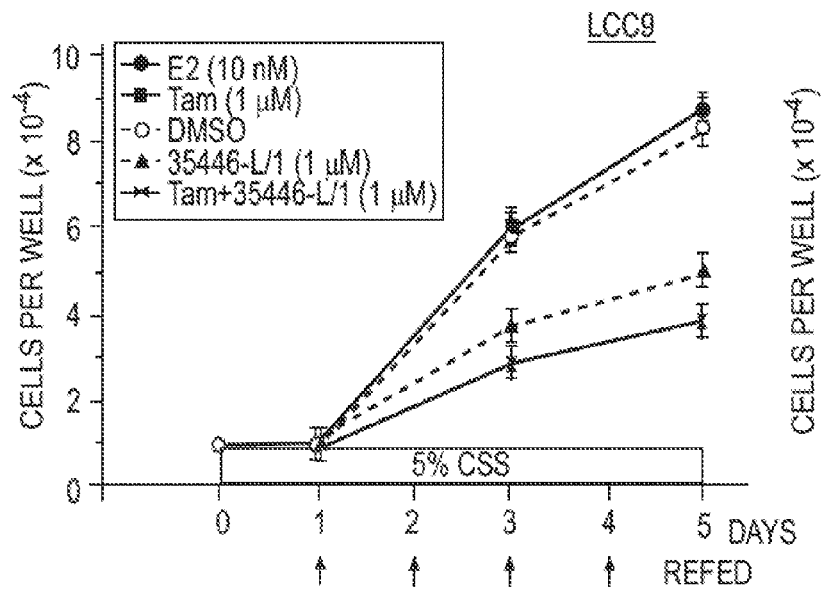
Figure 1D:
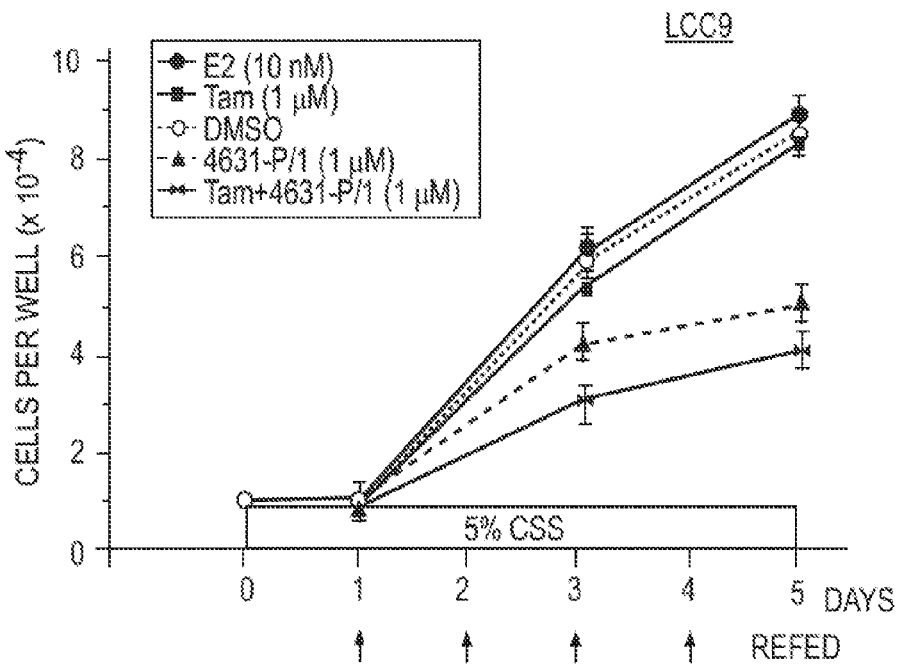

Tam-resistant LCC9 cells were seeded into 12-well dishes at $1 \times 10^4$ cells per well in DMEM containing 5% charcoal-stripped serum (CSS). Starting on Day 1 after allowing for attachment, the cells were fed daily with fresh medium containing 5% CSS and either vehicle (DMSO), E2 (10 nM), Tam (1 µM), a sensitizing compound (1 µM), or Tam+ the sensitizing compound. Triplicate wells were counted on Days 1, 3, and 5. Results are shown in FIGS. 1C and 1D, with values being expressed as means±SEMs.

Example 2

Toxicity of Sensitizing Compounds

Figure 2A:
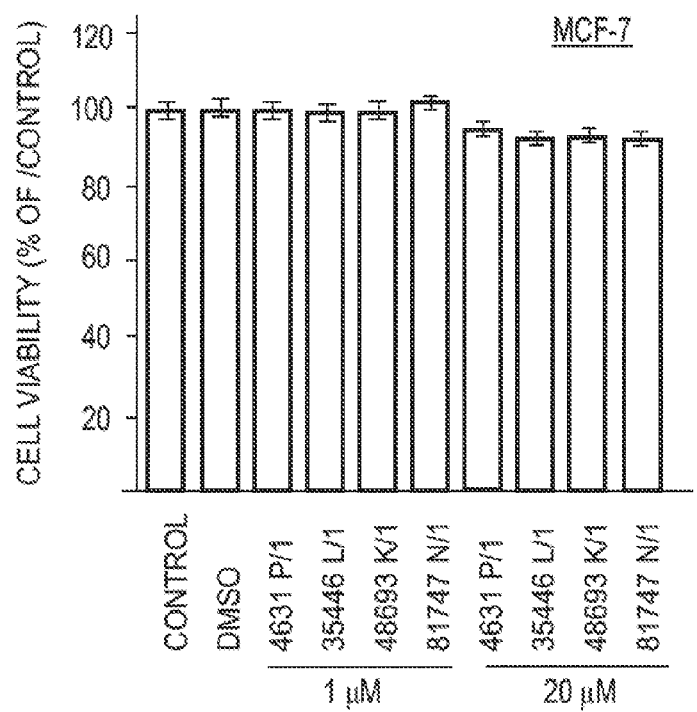
FIG. 2 depicts toxicity of the sensitizing compounds of the present invention on cells.
Figure 2B:
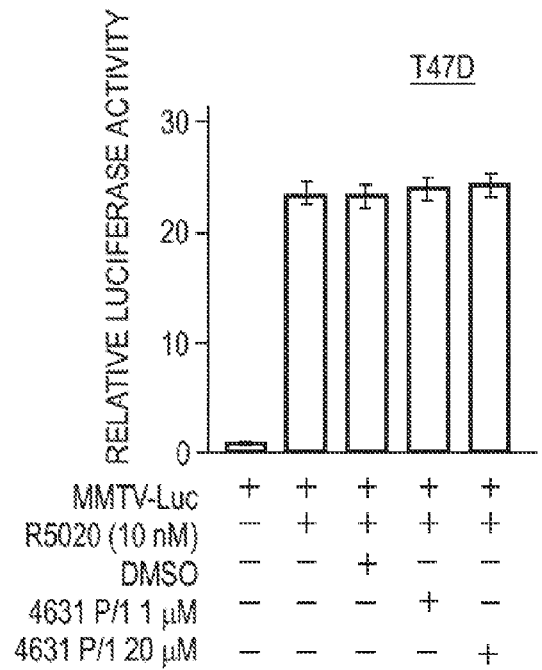
Figure 3A:
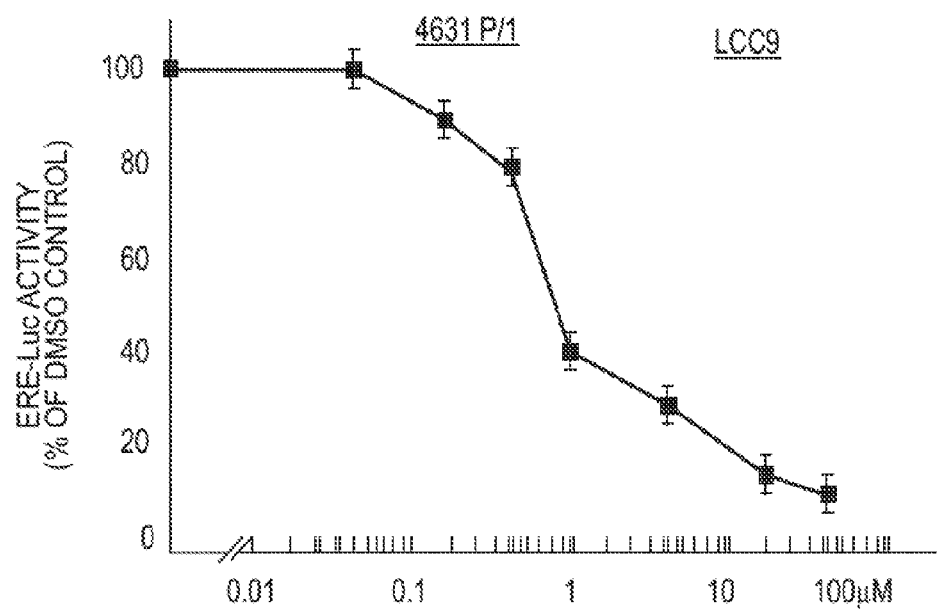
FIG. 3 depicts the inhibition of ER activity in anti-estrogen resistant LCC9 cells. LCC9 cells in 24-well dishes were transfected overnight with the ERE-TK-Luc reporter plasmid (0.25 μg per well), washed, and allowed to recover for several hours in fresh culture medium. The cells were then treated with the indicated concentrations of the six bioactive compounds or vehicle only (DMSO) for 24 hr and assayed for luciferase activity. Luciferase activity is expressed as a percentage of the DMSO control. Values are means±SEMs of four replicate wells.
Figure 3B:
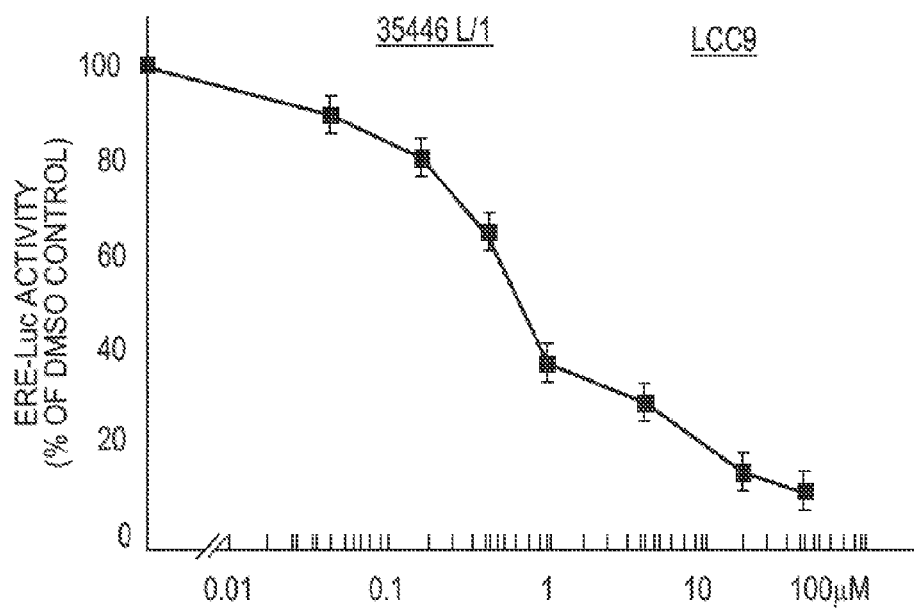
Figure 3C:
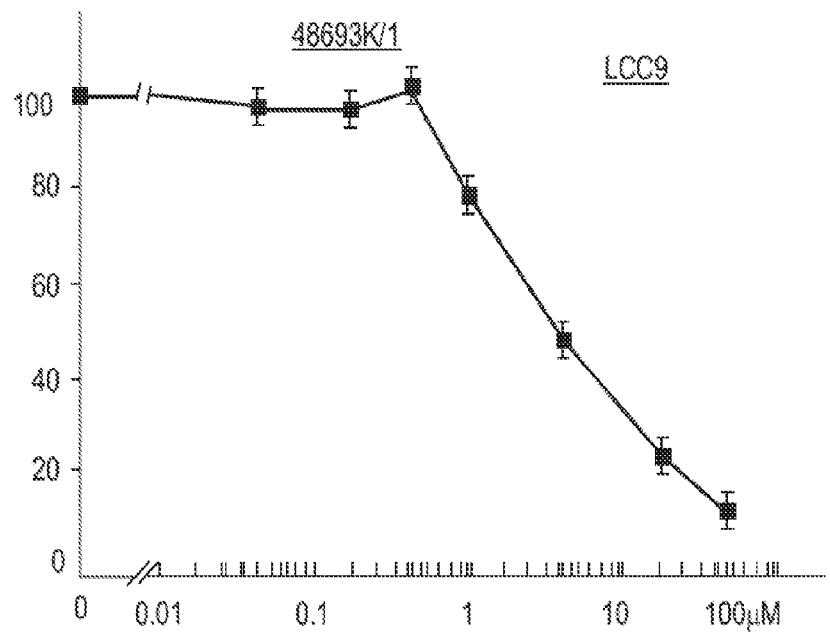
Figure 3D:
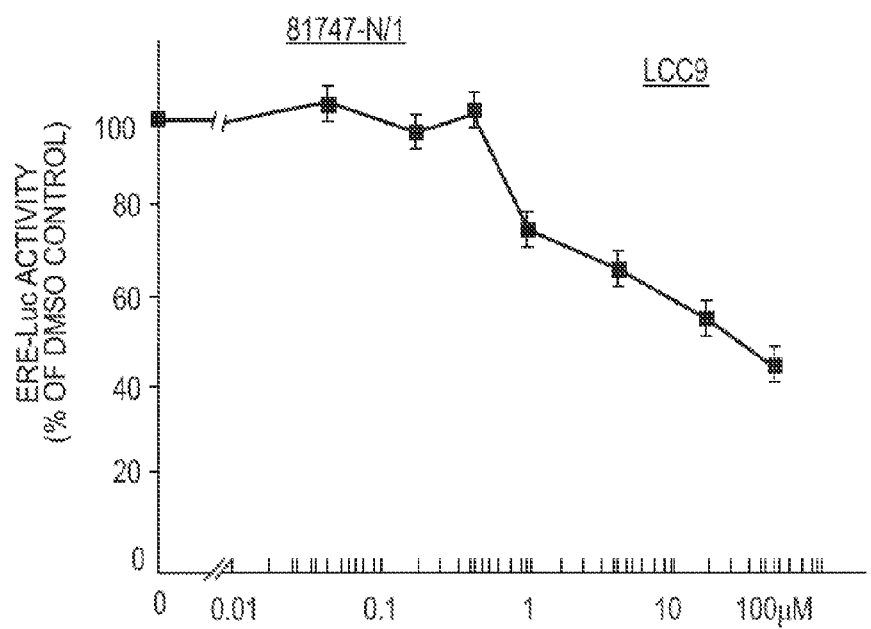
Figure 3E:
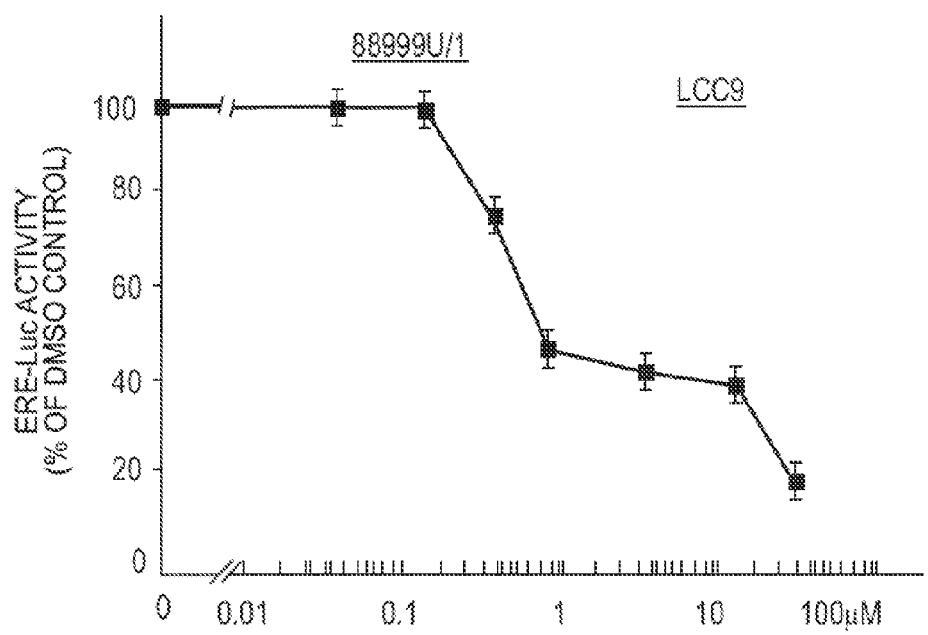
Figure 3F:
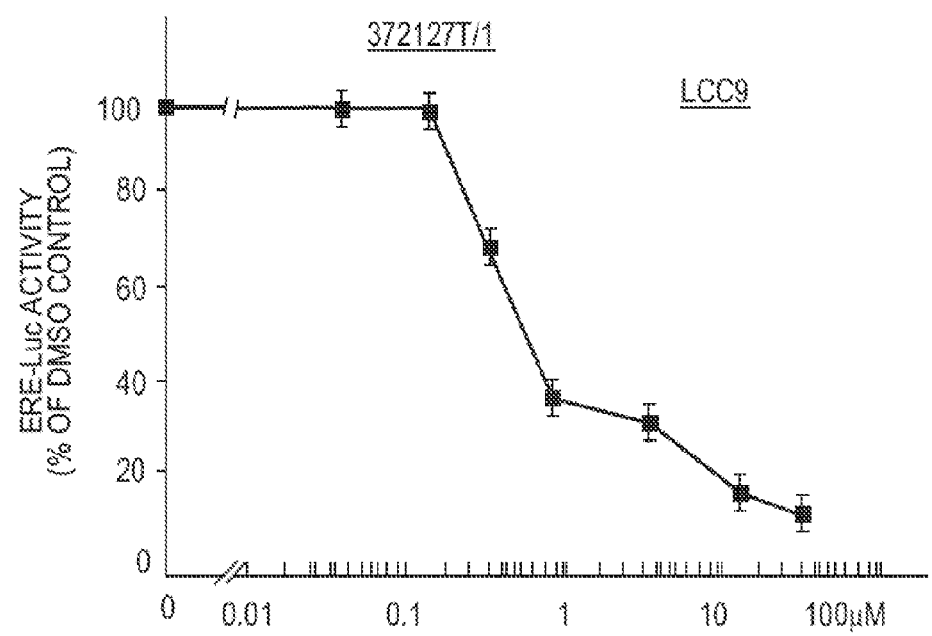
Figure 4A:
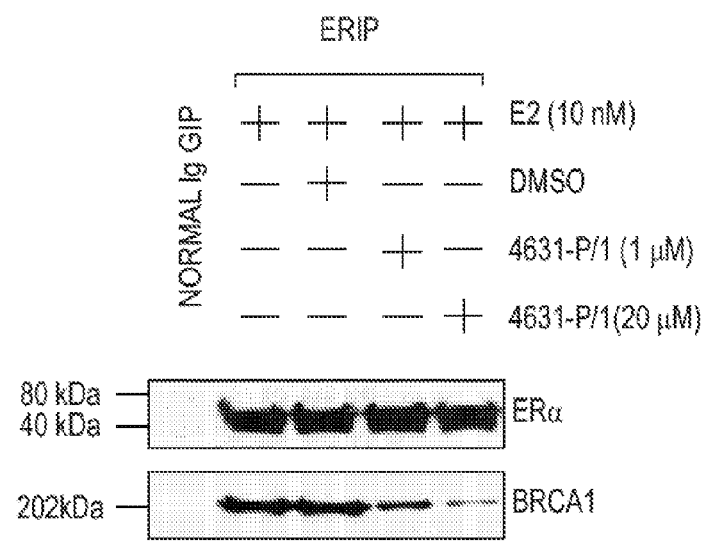
FIG. 4 depicts the ability of compound 4631-P/1 to disrupt the BRCA1:ER complex. (A and B) The ability of bioactive compound 4631-P/1 was tested for its ability to dissociate the BRCA1:ER-α complex by reciprocal immunoprecipitation (IP)-Western blotting. At 0, 1, and 20 µM, compound 4631-P/1 caused concentration-dependent dissociation of ER and BRCA1. As a negative control, a normal IgG IP failed to precipitate BRCA1 or ER. (C) Compound 4631-P/1 had no effect on the total cellular levels of ER or BRCA1, as indicated by Western blotting of non-precipitated lysates.
Figure 4B:
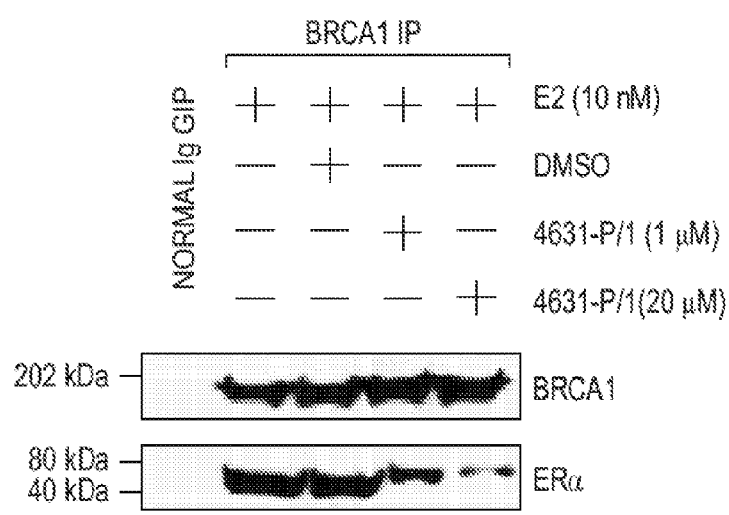
Figure 4C:
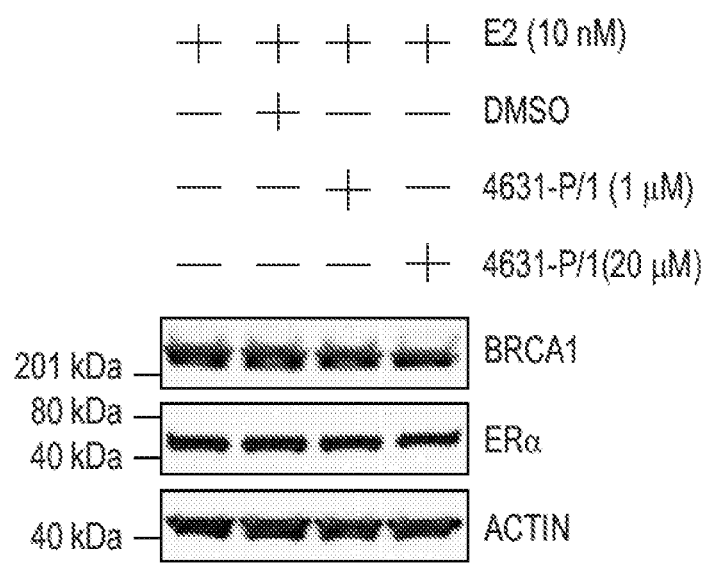
Figure 5A:
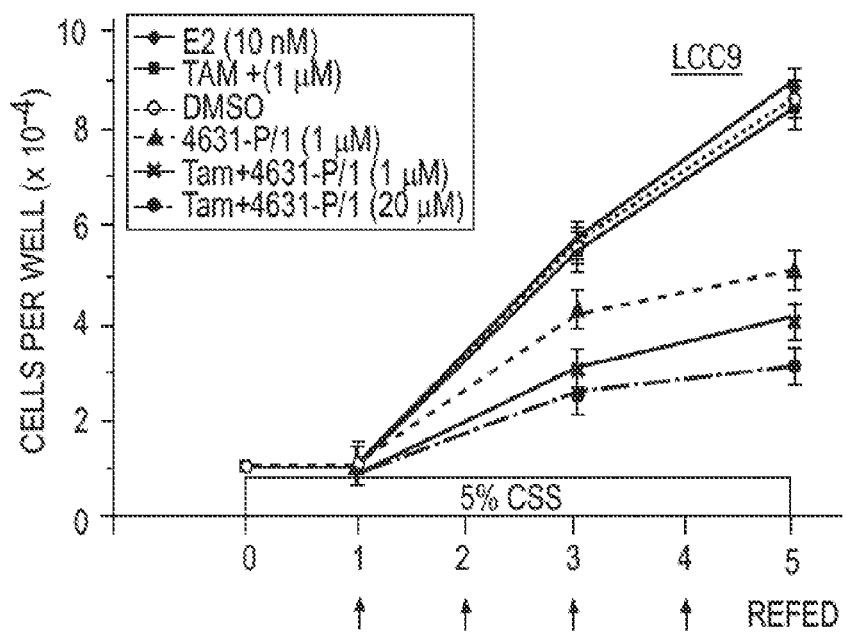
FIG. 5 depicts the ability of compounds 4631-P/1 and 35466-L/1 to inhibit proliferation of anti-estrogen resistant human breast carcinoma cells and partially restore their sensitivity to Tamoxifen. LCC9 cells (A,B,E,F) or LCC2 cells (C,D) were seeded into 12-well dishes at 1×10⁴ cells per well on day 0. Starting on day 1 (after allowing for cell attachment), the cells were refed daily with fresh medium (DMEM plus 5% charcoal-stripped serum (CSS)) containing the indicated agent(s). In panel F, the cells were refed with medium also containing ER-siRNA or control-siRNA (100 nM) at the indicated times. Wells were counted on at the indicate times to determine cell numbers. Values plotted are means±SEMs of triplicate wells.
Figure 5B:
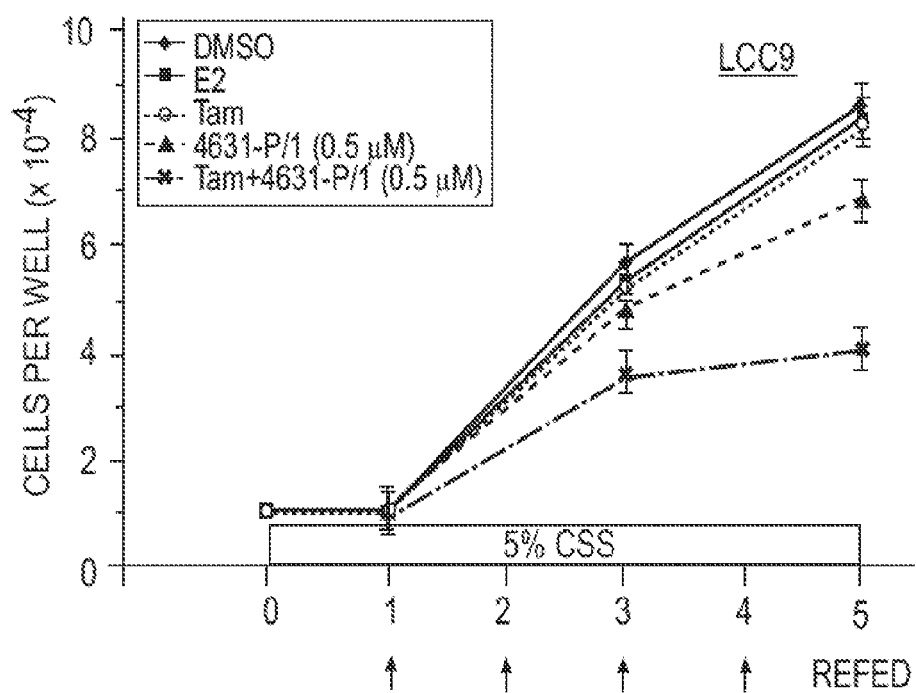
Figure 5C:
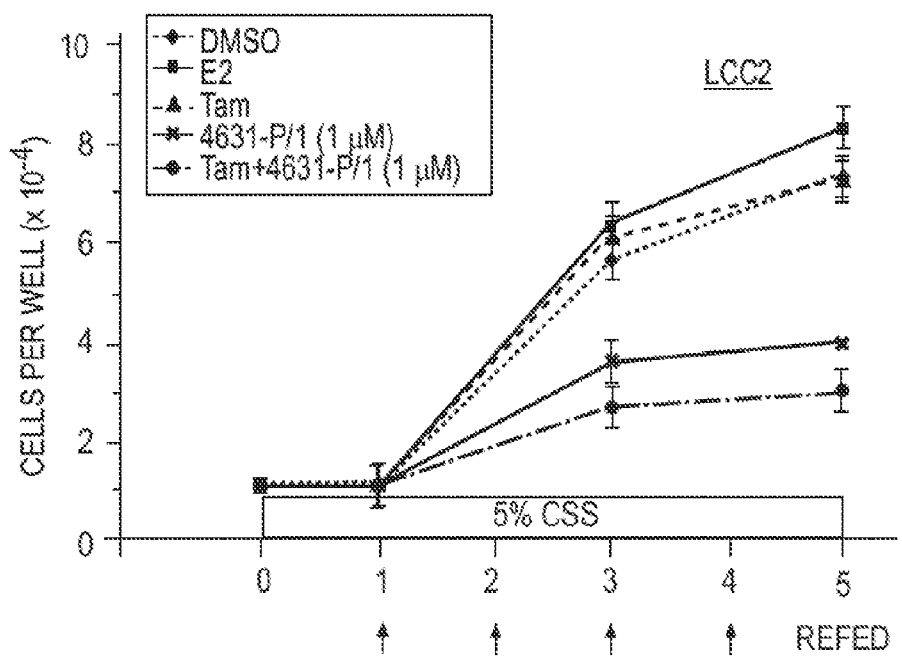
Figure 5D:
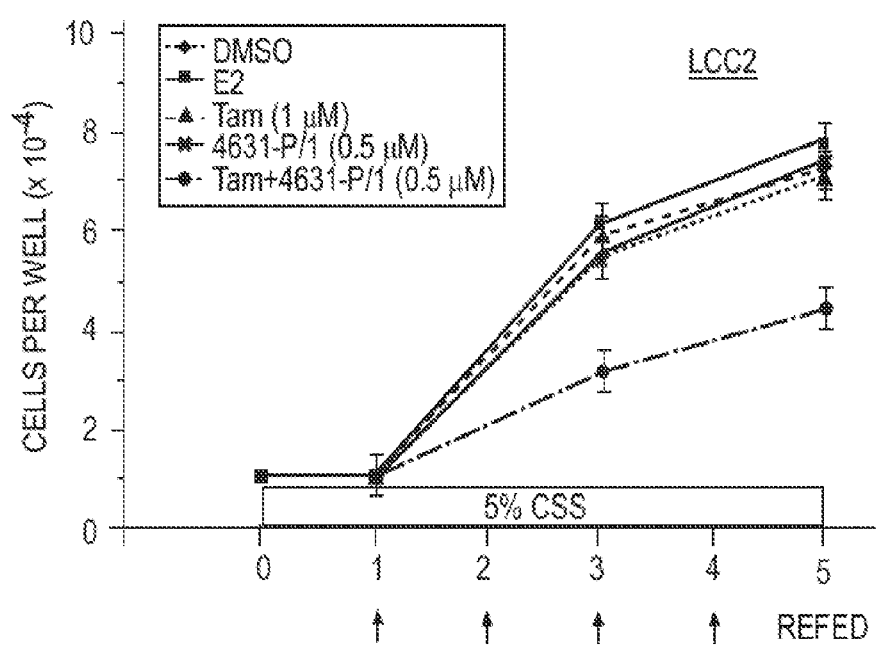
Figure 5E:
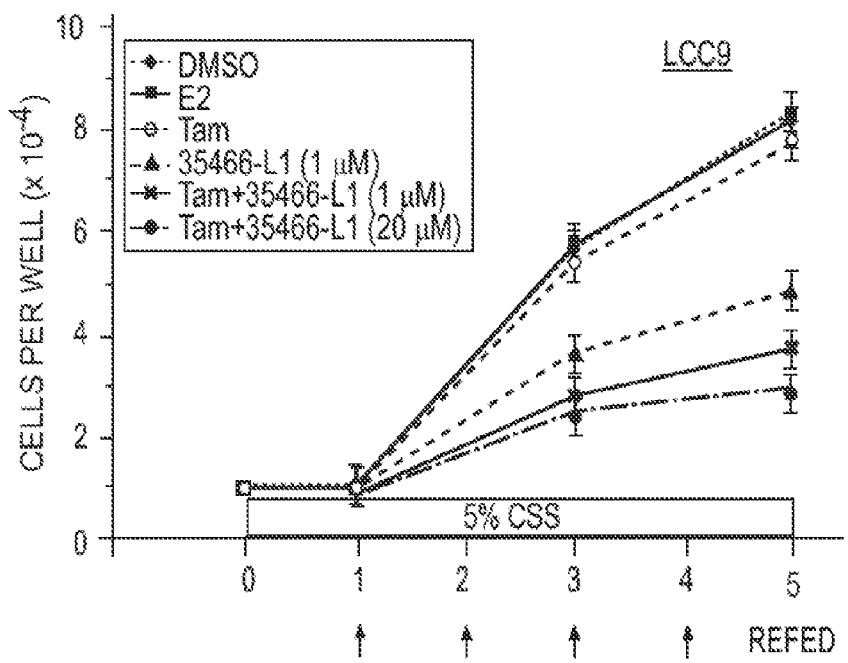
Figure 5F:
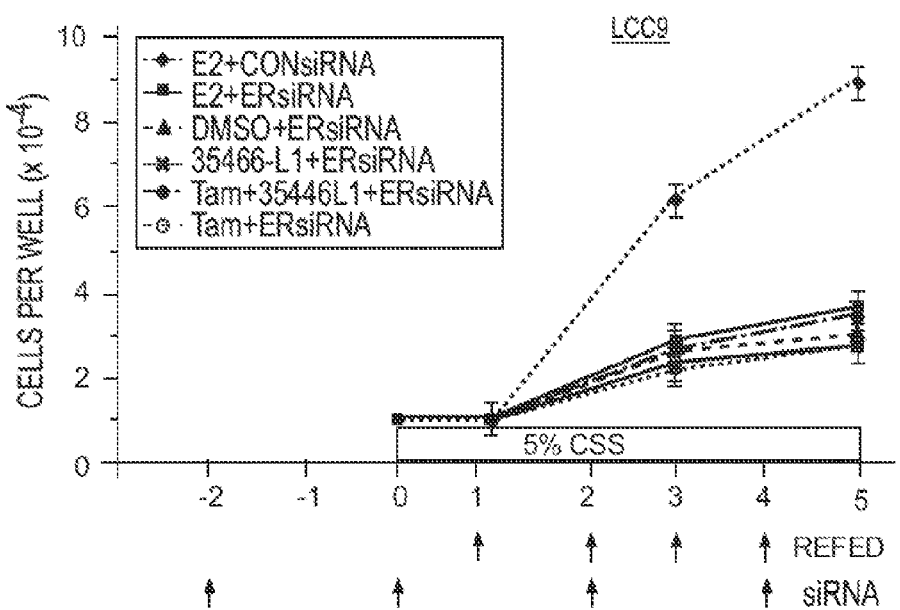
Figure 6A:
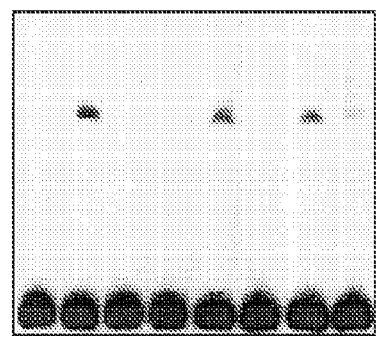
FIG. 6 depicts the ability of compound 4631-P/1 to disrupt the interaction of ER with a model ERE oligonucleotide in MCF-7 cells. (A,B) Briefly, MCF-7 cells in DMEM containing 5% charcoal-stripped serum were pre-incubated±E2 (10 nM) and with compound 4631-P/1 (0, 1, or 20 µM) or vehicle (DMSO) for 24-hr. After the 24-hr incubation, the cells were harvested, nuclear extracts were prepared, and the extracts were reacted with labeled "hot" ERE and an excess of unlabeled "cold" ERE, as indicated, prior to electrophoresis. In panel B, the experiment was performed similarly except that an anti-ER antibody was added to generate a "supershift." (C,D) These experiments were performed similarly to those in panels A and B, except that different concentrations of compound (as indicated) were added directly to the reaction mixture containing nuclear extract and were not pre-incubated with whole cells.
Figure 6B:
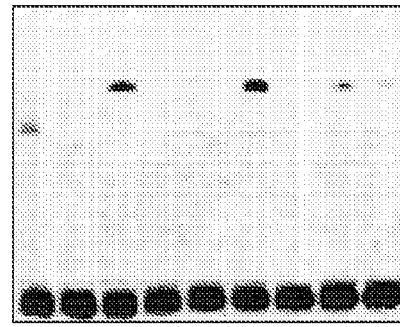
Figure 6C:
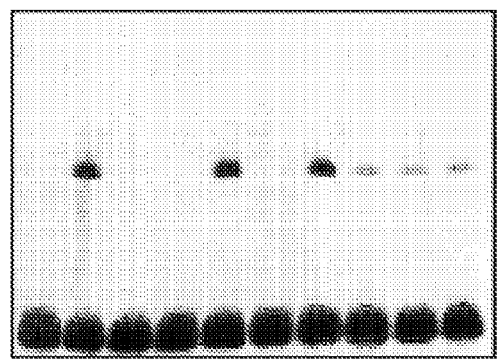
Figure 6D:
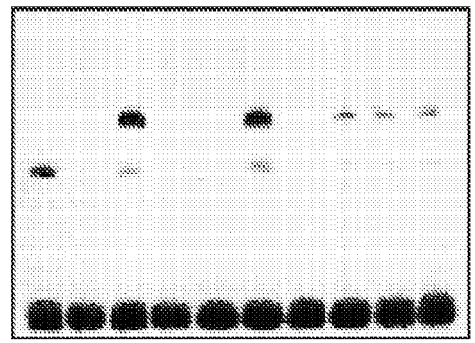
Figure 7A:
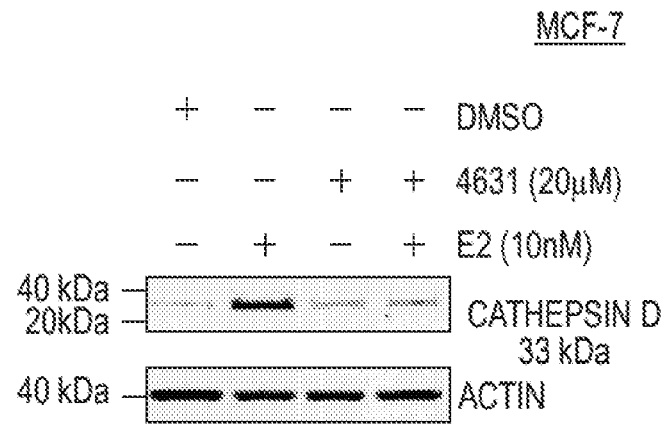
FIG. 7 depicts the ability of compounds 4631-P/1 and 35466-L/1 to inhibit the expression of an ER-regulated gene. Cathepsin D was used as a prototype E2/ER-regulated gene. In MCF-7 cells, basal cathepsin D protein levels were low, and were increased significantly by a 24-hr exposure to E2 (10 nM) (A and C). Compounds 4631-P/1 and 35466-L/1 alone had little or no effect on cathepsin D protein levels, but they effectively blocked the E2-stimulated expression of cathepsin D. On the other hand, LCC9 cells, which have a constitutively active ER expressed cathepsin D constitutively, and the high levels of cathepsin D protein were decreased significantly by a 24-hr exposure to compound either (B and D).
Figure 7B:
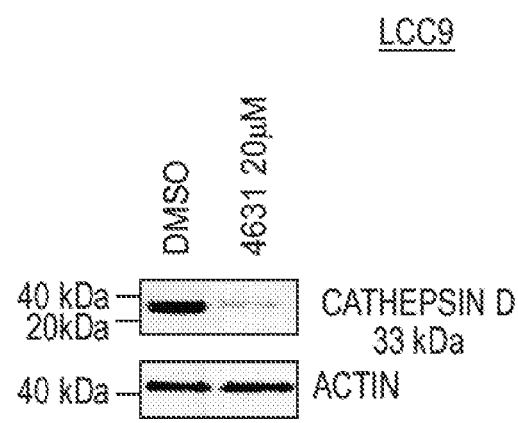
Figure 7C:
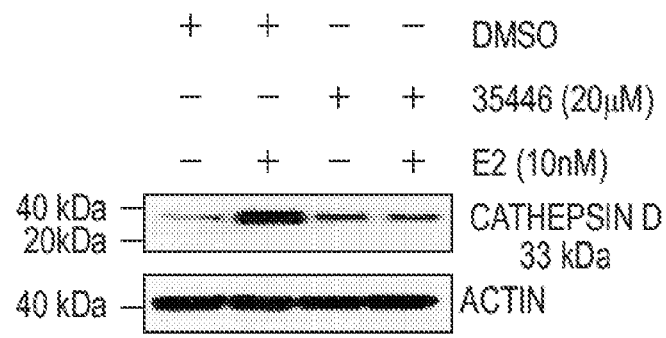
Figure 7D:
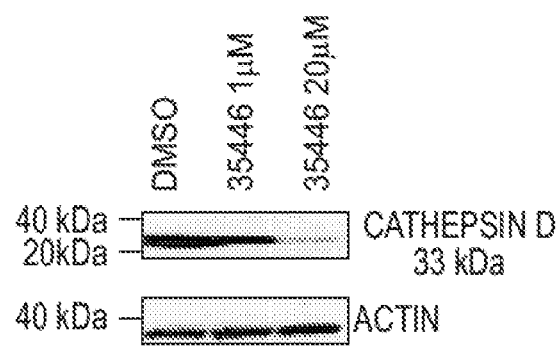
Figure 8A:
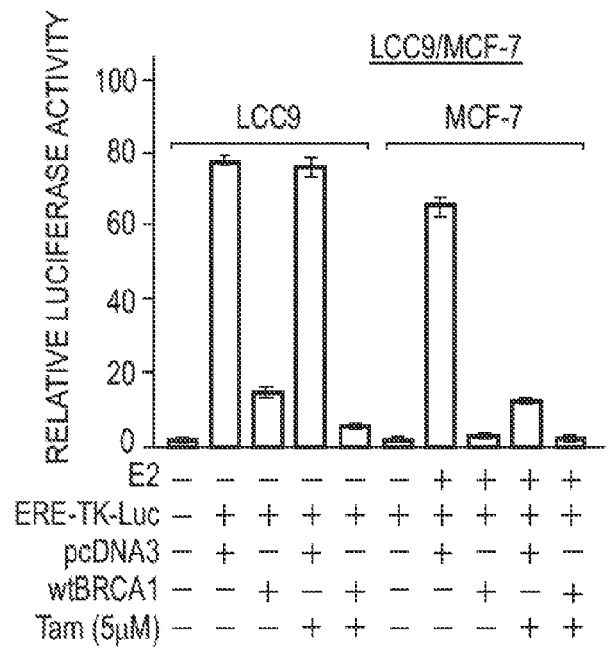
FIG. 8 depicts BRCA1 over-expression partially restores Tamoxifen sensitivity to anti-estrogen-resistant LCC9 cells. The effect of BRCA1 over-expression (by transfection of a wild-type (wt) full-length BRCA1 expression vector) was studied in E2-insensitive anti-estrogen resistant LCC9 human breast cancer cells with E2-sensitive/anti-estrogen sensitive MCF-7 breast cancer cells. The wtBRCA1 suppressed the constitutive ER activity (measured using the ERE-TK-Luc reporter as a readout), but Tam (5 µM) by itself had no effect on ER activity (A and B (left)). In each case, the combination of wtBRCA1+Tam gave greater suppression of ER activity than wtBRCA1 alone (P<0.001, two-tailed t-tests). In contrast to LCC9, wtBRCA1 and Tam each strongly suppressed E2-stimulated ER activity in MCF-7 cells. When MCF-7 cells were tested in the absence of E2, ER activity was very low under most conditions (illustrating the requirement for E2 to activate ER), but in the absence of E2, Tam functioned as an ER agonist and caused about a (5-6)-fold increase in ER activity (P<0.001). These findings show that BRCA1 over-expression not only inhibits ER activity in anti-estrogen resistant LCC9 cells but also partially restores sensitivity to Tam.
Figure 8B:
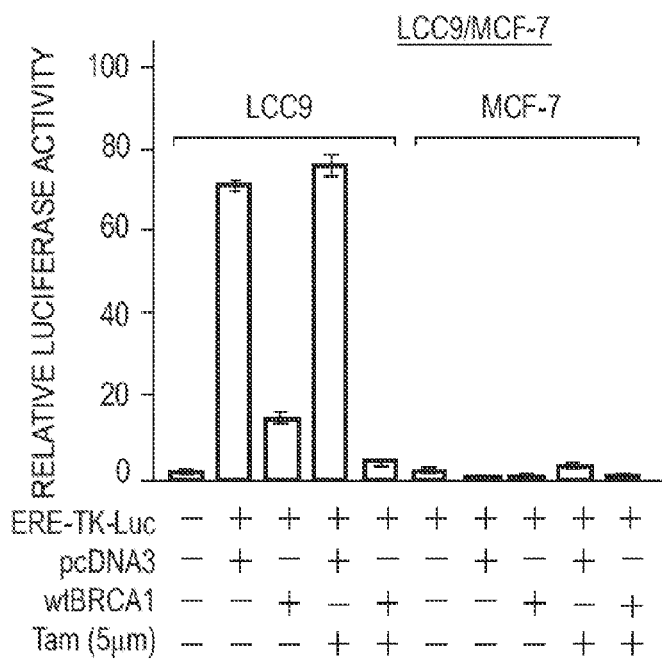
Figure 9A:
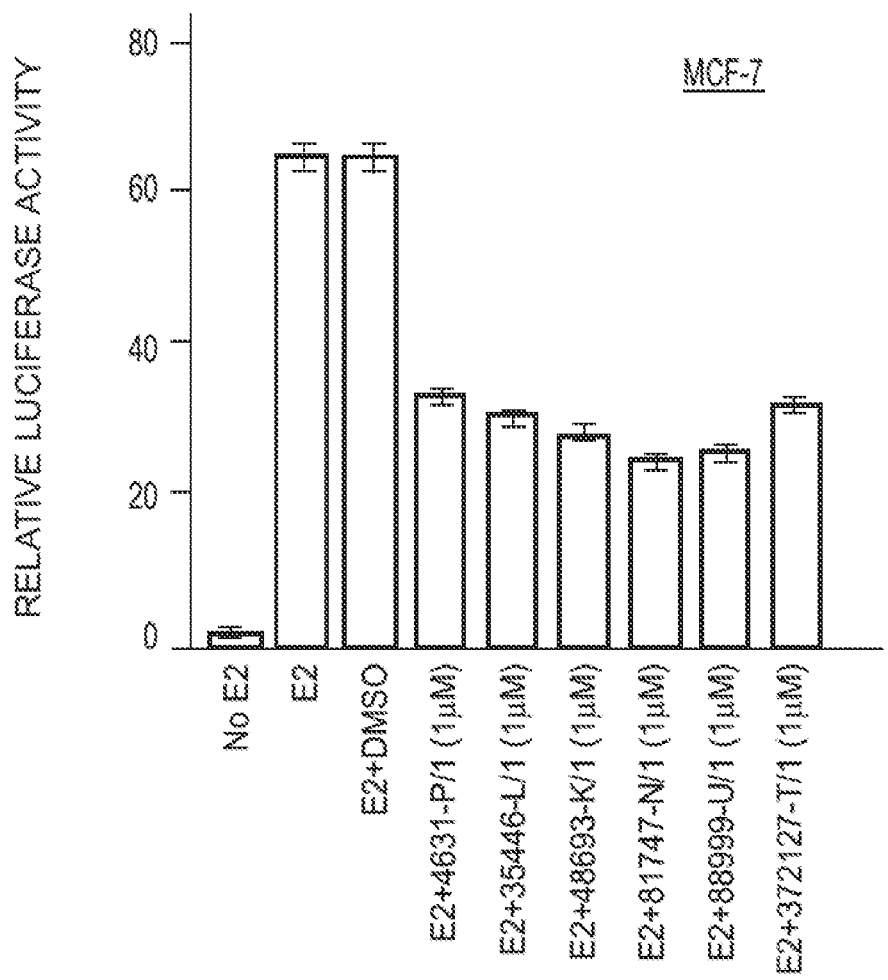
FIG. 9 depicts the inhibition of E2-stimulated ER activity in MCF-7 cells by six compounds.
Figure 10A:
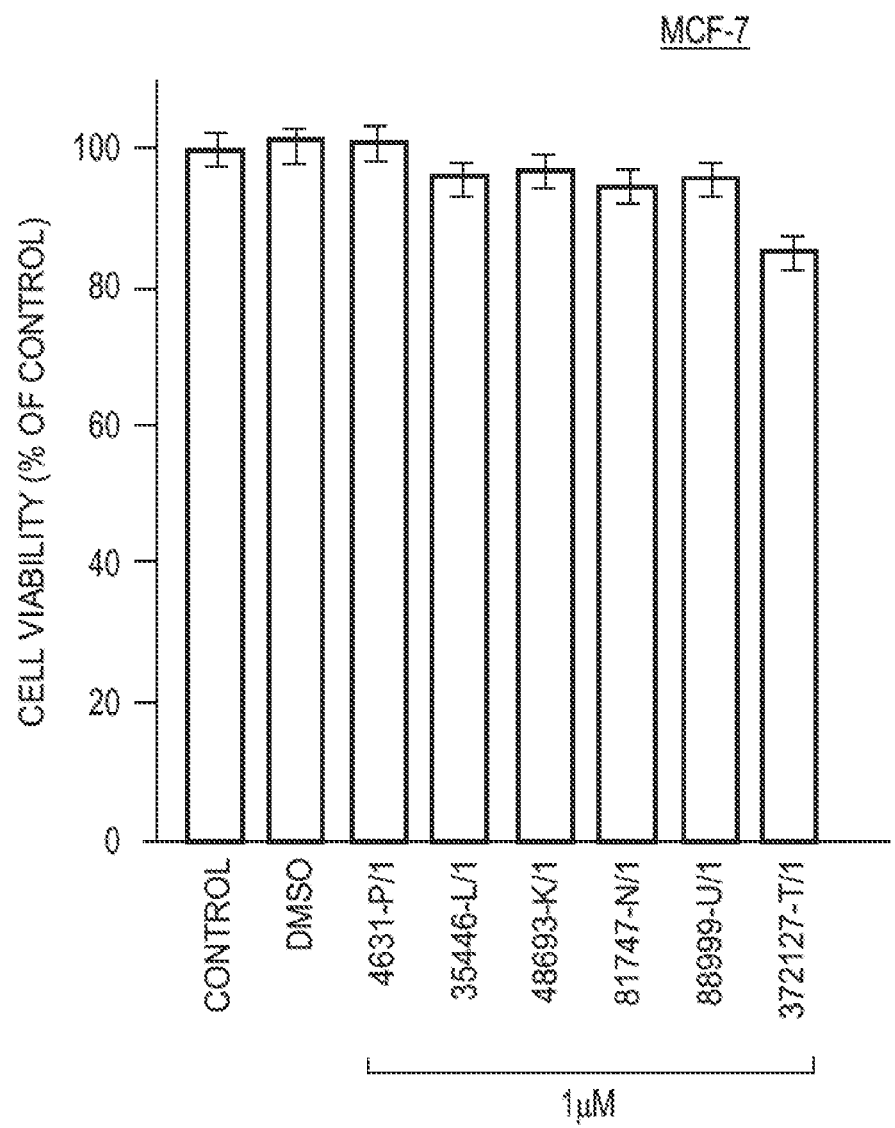
FIG. 10 depicts that the inhibition of ER activity by these six compounds is not to due to non-specific cytotoxicity, since cell viability remained over 80% after a 24-hr exposure to 1 µM of each of the compounds (A). One of the compounds was tested for its ability to inhibit progestin-stimulated progesterone receptor (PR) activity in a PR+ human breast cancer cell line (T47D), using the MMTV-Luc reporter as a readout for PR activity (B). Here, PR activity was stimulated over 20-fold by the synthetic progestin R5020 (10 nM), but compound 4631-P/1 had no effect on PR activity at either 1 µM or 20 µM.
Figure 10B:
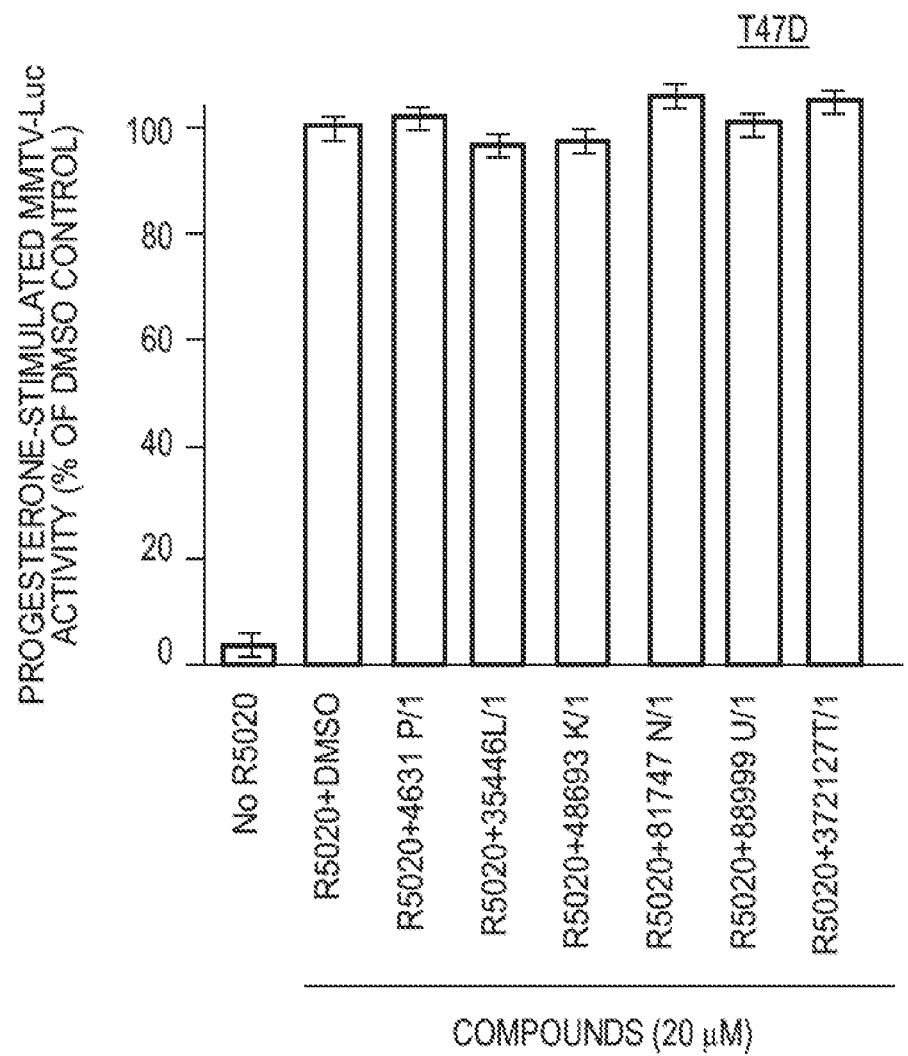
Figure 11A:
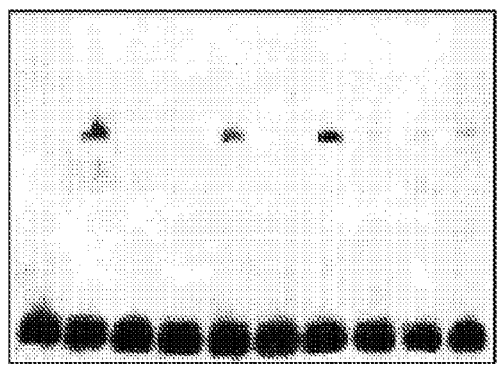
FIG. 11 (A and B) depict shift and supershift experiments, respectively, in which compound 35466-L/1 was not present during the incubation of the cells with E2 but was only added to the final reaction mixtures after the nuclear extracts were prepared. These experiments show that even when added to cell lysates, but not intact cells, 35466-L/1 can disrupt the association of ER with the consensus ERE.
Figure 11B:
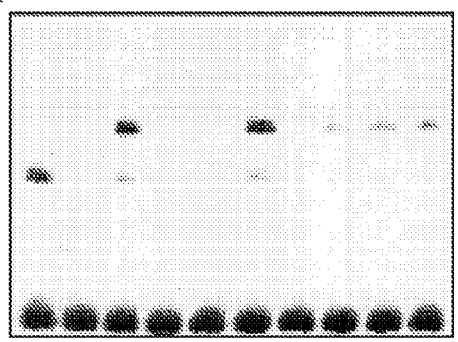

Subconfluent proliferating MCF-7 cells were treated with vehicle (DMSO) or with the a sensitizing compound for 24 hours and then assayed for cell viability using MTT dye reduction assays. FIG. 2A shows the results, with values of cell viability being represented as means±SEMs of ten replicate wells. Subconfluent proliferating T47D cells were also transfected overnight with a progesterone-responsive reporter (MMTV-Luc) and then exposed to a synthetic progestin (R5020, 10 nM) for 24 hours in the absence or presence of compound 4631 P/1, as indicated. FIG. 2B shows the results, with luciferase values being expressed relative to the negative control (no R5020 or compound) as means±SEMs of four replicate wells.

Example 3

Effects of Compounds on Tumor Growth

Studies are performed on 4-6 week old female (ovariectomized) NCr nu/nu mice. Mice receive one mammary fat pad inoculation of $5\times10^6$ tumor cells in 100 μl of cell culture medium. Endpoints are tumor growth delay and tumor doubling time (Td). Tumor area is recorded every 2-3 days by measuring the longest axis and perpendicular width. Td is determined with Gompertzian transformation. Mice will be weighed at the same time as the tumors are measured, to rule out the possibility that tumor shrinkage is related to caloric restriction. Treatment begins when tumors reach 0.5 cm. The dose is set to ⅓ of the multidose maximum tolerated dose (MTD), which will have been established in pilot studies. Four groups of animals will be studied, one receiving the sensitizing compound, one receiving an anti-estrogen therapy alone, one receiving anti-estrogen therapy plus the sensitizing compound and the final group receiving vehicle only (control).

At the end of the study, organs and tumors are removed for histologic examination and measurement of concentrations of compounds. For tumor growth delay, the times for treated (T) and control (C) tumors to reach a fixed size are measured. The growth delay=(T–C)/C where the T/C or T–C are median values.

What is claimed is:

1. A method of treating breast cancer in a subject, the method comprising administering to a subject in need of treatment thereof a therapeutically effective amount of at least one sensitizing compound selected from the group consisting of:

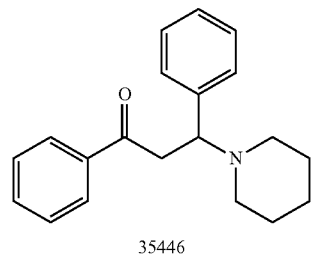 [SMILES: O=C(CC(c1ccccc1)N1CCCCC1)c1ccccc1]

35446 or a pharmaceutically acceptable salt thereof.

2. The method of claim 1, further comprising administering an anti-estrogen compound to the subject.

3. The method of claim 2, wherein the anti-estrogen compound is a selective estrogen receptor modulator (SERM) or a selective estrogen receptor down regulator (SERD).

4. The method of claim 3, wherein the anti-estrogen compound is a SERM.

5. The method of claim 4, wherein the SERM is a tamoxifen-like compound or raloxifene.

6. The method of claim 5, wherein the tamoxifen-like compound is tamoxifen, 4-hydroxytamoxifen or 4-desmethyl-4-hydroxytamoxifen.

7. The method of claim 3, wherein the anti-estrogen compound is a SERD.

8. The method of claim 7, wherein the SERD is fulvestrant.

9. The method of claim 2, wherein the anti-estrogen compound and the at least one sensitizing compound are administered simultaneously to the subject.

10. The method of claim 9, wherein the breast cancer in the subject is resistant to at least one anti-estrogen therapy.

* * * * *